ated under 35
(12) United States Patent
Mello et al.

(10) Patent No.: US 9,579,269 B2
(45) Date of Patent: Feb. 28, 2017

(54) THERAPEUTIC ORAL COMPOSITION

(75) Inventors: Sarita V. Mello, North Brunswick, NJ (US); Evangelia Arvanitidou, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 486 days.

(21) Appl. No.: 13/701,844

(22) PCT Filed: Jun. 23, 2010

(86) PCT No.: PCT/US2010/039677
§ 371 (c)(1),
(2), (4) Date: Dec. 4, 2012

(87) PCT Pub. No.: WO2011/162756
PCT Pub. Date: Dec. 29, 2011

(65) Prior Publication Data
US 2013/0078197 A1 Mar. 28, 2013

(51) Int. Cl.
| | |
|---|---|
| A61K 8/44 | (2006.01) |
| A61Q 11/00 | (2006.01) |
| A61K 8/19 | (2006.01) |
| A61K 8/27 | (2006.01) |
| A61K 8/73 | (2006.01) |
| A61K 8/81 | (2006.01) |
| A61Q 17/00 | (2006.01) |
| A61K 9/00 | (2006.01) |
| A61K 9/06 | (2006.01) |

(52) U.S. Cl.
CPC .................. *A61K 8/44* (2013.01); *A61K 8/19* (2013.01); *A61K 8/27* (2013.01); *A61K 8/73* (2013.01); *A61K 8/731* (2013.01); *A61K 8/8147* (2013.01); *A61K 8/8164* (2013.01); *A61K 8/8182* (2013.01); *A61Q 11/00* (2013.01); *A61Q 17/005* (2013.01); *A61K 9/006* (2013.01); *A61K 9/06* (2013.01)

(58) Field of Classification Search
USPC .......................................................... 424/52
See application file for complete search history.

(56) References Cited

U.S. PATENT DOCUMENTS

| | | |
|---|---|---|
| 3,535,421 A | 10/1970 | Briner et al. |
| 3,538,230 A | 11/1970 | Pader et al. |
| 3,678,154 A | 7/1972 | Widder et al. |
| 3,683,006 A | 8/1972 | Fried |
| 3,696,191 A | 10/1972 | Weeks |
| 3,862,307 A | 1/1975 | DiGiulio |
| 3,925,543 A | 12/1975 | Donohue |
| 3,932,605 A | 1/1976 | Vit |
| 3,932,608 A | 1/1976 | Anderson et al. |
| 3,937,807 A | 2/1976 | Haefele |
| 3,943,241 A | 3/1976 | Anderson et al. |
| 3,959,458 A | 5/1976 | Agricola et al. |
| 3,988,434 A | 10/1976 | Schole et al. |
| 3,991,177 A | 11/1976 | Vidra et al. |
| 4,011,309 A | 3/1977 | Lutz |
| 4,022,880 A | 5/1977 | Vinson et al. |
| 4,025,616 A | 5/1977 | Haefele |
| 4,042,680 A | 8/1977 | Muhler et al. |
| 4,051,234 A | 9/1977 | Gieske et al. |
| 4,058,595 A | 11/1977 | Colodney |
| 4,064,138 A | 12/1977 | Saari et al. |
| 4,100,269 A | 7/1978 | Pader |
| 4,108,979 A | 8/1978 | Muhler et al. |
| 4,108,981 A | 8/1978 | Muhler et al. |
| 4,138,477 A | 2/1979 | Gaffar |
| 4,146,607 A | 3/1979 | Ritchey |
| 4,154,813 A | 5/1979 | Kleinberg |
| 4,154,815 A | 5/1979 | Pader |
| 4,160,821 A | 7/1979 | Sipos |
| 4,177,258 A | 12/1979 | Gaffar et al. |
| 4,213,961 A | 7/1980 | Curtis et al. |
| 4,225,579 A | 9/1980 | Kleinberg |
| 4,226,851 A | 10/1980 | Sompayrac |
| 4,259,316 A | 3/1981 | Nakashima et al. |
| 4,269,822 A | 5/1981 | Pellico et al. |
| 4,292,304 A | 9/1981 | Barels et al. |
| 4,305,928 A | 12/1981 | Harvey |
| 4,335,102 A | 6/1982 | Nakashima et al. |
| 4,339,432 A | 7/1982 | Ritchey et al. |
| 4,340,583 A | 7/1982 | Wason |

(Continued)

FOREIGN PATENT DOCUMENTS

| | | |
|---|---|---|
| EP | 0569666 | 11/1993 |
| EP | 1358872 | 11/2003 |
| ES | 2300399 | 6/2008 |
| GB | 2354441 | 3/2001 |
| JP | 60-092208 A | 5/1985 |
| JP | H03128316 | 5/1991 |
| JP | 07-258053 A | 10/1995 |
| JP | 08-151324 | 6/1996 |
| JP | 2005-029484 | 2/2005 |
| SU | 1754104 | 8/1992 |

(Continued)

OTHER PUBLICATIONS

Craig et al., 1999, "The antibacterial effects of tumescent liposuction fluid," Plast. Reconstr. Surg., 103(2):666-70 (Abstract).

Craig et al., 1985, Restorative Dental Materials, Seventh Edition Chapter 9: Amalgam, pp. 198-224, C. V. Mosby Company, St. Louis.

(Continued)

*Primary Examiner* — Walter Webb

(57) ABSTRACT

Disclosed are therapeutic oral compositions useful in the treatment of a variety of oral disorders, in which the composition can provide blockage of dentinal tubes, while at the same time provide antibacterial and anti-caries efficacy. The compositions include arginine in free or salt form, a mucoadhesive polymer, and at least one component selected from pyrophosphates, zinc salts, potassium salts, strontium salts, and mixtures thereof.

8 Claims, No Drawings

(56) References Cited

U.S. PATENT DOCUMENTS

| | | | |
|---|---|---|---|
| 4,355,022 | A | 10/1982 | Rabussay |
| RE31,181 | E | 3/1983 | Kleinberg |
| 4,422,985 | A | 12/1983 | Morishita et al. |
| 4,426,337 | A | 1/1984 | Suzuki et al. |
| 4,466,954 | A | 8/1984 | Ichikawa et al. |
| 4,521,551 | A | 6/1985 | Chang et al. |
| 4,528,181 | A | 7/1985 | Morton et al. |
| 4,532,124 | A | 7/1985 | Pearce |
| 4,538,990 | A | 9/1985 | Pashley |
| 4,606,912 | A | 8/1986 | Rudy et al. |
| 4,631,185 | A | 12/1986 | Kim |
| 4,645,662 | A | 2/1987 | Nakashima et al. |
| 4,656,031 | A | 4/1987 | Lane et al. |
| 4,721,614 | A | 1/1988 | Winston et al. |
| 4,725,576 | A | 2/1988 | Pollock et al. |
| 4,751,072 | A | 6/1988 | Kim |
| 4,842,847 | A | 6/1989 | Amjad |
| 4,866,161 | A | 9/1989 | Sikes et al. |
| 4,885,155 | A | 12/1989 | Parran, Jr. et al. |
| 4,992,420 | A | 2/1991 | Neeser |
| 4,997,640 | A | 3/1991 | Bird et al. |
| 5,000,939 | A | 3/1991 | Dring et al. |
| 5,004,597 | A | 4/1991 | Majeti et al. |
| 5,028,432 | A | 7/1991 | Chopra et al. |
| 5,094,842 | A | 3/1992 | Riley |
| 5,096,700 | A | 3/1992 | Seibel et al. |
| 5,139,768 | A | 8/1992 | Friedman |
| 5,160,737 | A | 11/1992 | Friedman et al. |
| 5,188,821 | A | 2/1993 | Gaffar et al. |
| 5,192,530 | A | 3/1993 | Gaffar et al. |
| 5,197,531 | A | 3/1993 | Hugo et al. |
| 5,286,480 | A | 2/1994 | Boggs et al. |
| 5,334,375 | A | 8/1994 | Nabi et al. |
| 5,334,617 | A | 8/1994 | Ulrich et al. |
| 5,370,865 | A | 12/1994 | Yamagishi et al. |
| 5,390,984 | A | 2/1995 | Boucherie et al. |
| 5,393,796 | A | 2/1995 | Halberstadt et al. |
| 5,478,570 | A | 12/1995 | Sunohara et al. |
| 5,533,791 | A | 7/1996 | Boucherie |
| 5,543,443 | A | 8/1996 | Rajaiah et al. |
| 5,561,177 | A | 10/1996 | Khaledi et al. |
| 5,571,502 | A | 11/1996 | Winston et al. |
| 5,589,159 | A | 12/1996 | Markowitz et al. |
| 5,609,890 | A | 3/1997 | Boucherie |
| 5,639,795 | A | 6/1997 | Friedman et al. |
| 5,747,004 | A | 5/1998 | Giani et al. |
| 5,762,911 | A | 6/1998 | Kleinberg et al. |
| 5,906,811 | A | 5/1999 | Hersh |
| 5,922,346 | A | 7/1999 | Hersh |
| 5,997,301 | A | 12/1999 | Linden |
| 6,217,851 | B1 | 4/2001 | Kleinberg et al. |
| 6,306,435 | B1 | 10/2001 | Chen et al. |
| 6,436,370 | B1 * | 8/2002 | Kleinberg et al. ............... 424/49 |
| 6,488,961 | B1 | 12/2002 | Robinson et al. |
| 6,524,558 | B2 | 2/2003 | Kleinberg et al. |
| 6,558,654 | B2 | 5/2003 | McLaughlin |
| 6,696,045 | B2 | 2/2004 | Yue et al. |
| 6,850,883 | B1 | 10/2004 | Chevaus et al. |
| 7,087,219 | B2 | 8/2006 | Burzynski et al. |
| 7,166,272 | B2 | 1/2007 | Fujisawa |
| 2002/0081360 | A1 | 6/2002 | Burgard et al. |
| 2005/0031551 | A1 | 2/2005 | Prencipe et al. |
| 2007/0053849 | A1 | 3/2007 | Doyle et al. |
| 2007/0258916 | A1 | 11/2007 | Ferracane et al. |
| 2008/0233054 | A1 | 9/2008 | Kleinberg et al. |
| 2008/0267891 | A1 * | 10/2008 | Zaidel et al. ................ 424/50 |
| 2008/0286214 | A1 | 11/2008 | Brown et al. |
| 2009/0186090 | A1 | 7/2009 | Zaidel et al. |
| 2009/0202450 | A1 * | 8/2009 | Prencipe et al. ............... 424/50 |
| 2009/0202454 | A1 | 8/2009 | Prencipe et al. |
| 2009/0202456 | A1 | 8/2009 | Prencipe et al. |
| 2009/0202465 | A1 | 8/2009 | Mougin et al. |
| 2009/0311200 | A1 | 12/2009 | Lambert et al. |
| 2009/0320226 | A1 | 12/2009 | Robinson et al. |
| 2010/0135932 | A1 | 6/2010 | Deckner et al. |

FOREIGN PATENT DOCUMENTS

| | | |
|---|---|---|
| WO | WO 97/32565 | 9/1997 |
| WO | WO 01/85116 | 11/2001 |
| WO | WO 03/043593 | 5/2003 |
| WO | WO 2004/082628 | 9/2004 |
| WO | WO 2007/011552 | 1/2007 |
| WO | WO 2007/068916 | 6/2007 |
| WO | WO 2008/069622 | 6/2008 |
| WO | WO 2009/099435 | 8/2009 |
| WO | WO 2009/099451 | 8/2009 |
| WO | WO 2009/099455 | 8/2009 |
| WO | WO 2009/100264 | 8/2009 |
| WO | WO 2009/100277 | 8/2009 |
| WO | WO 2009/149030 | 12/2009 |
| WO | WO 2009/152507 | 12/2009 |
| WO | WO 2009/157956 | 12/2009 |
| WO | WO 2010/115041 | 10/2010 |

OTHER PUBLICATIONS

Chatterjee et al, "Bacterial Acidification and CaviStat Alkalinization of Occlusal Fissure pH," 83rd Session of the American Association for Dental Research, Mar. 9-12, 2005, Baltimore, Maryland.

Dewhirst, 1980, "Structure-Activity Relationships for Inhibition of Prostaglandin Cyclooxygenase by Phenolic Compounds," Prostaglandins, 20(2):209-222.

DenClude Desensitizing Dental Cream Internet Article, 2007, http://www.colgateprofessional.com/LeadershipUS/Products/Docs/DenClude_Datasheet.pdf.

Gaffar et al., 1990, "Antiplaque Effects of Dentifrices Containing Triclosan/Copolymer/NaF Systems Versus Triclosan Dentifrices without the Copolymer," American J. Dentistry 3:S7-S-14.

Grove et al., 2003, "Improving the Aqueous Solubility of Triclosan by Solubilization, Complexation, and in situ Salt Formation," J. Cosmetic Science 54(6):537-550.

Kleinberg, 1999, "A New Saliva-Based Anticaries Composition", Dentistry Today, 18:2.

Kleinberg, 2002, "A Mixed-Bacteria Ecological Approach to Understanding the Role of the Oral Bacteria in Dental Caries Causation: An Alternative to Streptococcus mutans and the Specific-Plaque Hypothesis," Crit. Rev. Oral Biol. Med., pp. 108-125, 12:2.

Machado et al., "CaviStat Confection Inhibition of Caries in Posterior Teeth," 83rd Session of the American Association for Dental Research, Mar. 21-24, 2007, New Orleans, Louisiana (Abstract).

Nouri, et al., 2003, "Paediatrics: A Review of the Antibacterial Effect of Fluoride," Oral Health Group, pp. 1-7.

Ofner et al., 1987, "Swelling studies of gelatin. II: Effect of additives," J. Pharm. Sci., vol. 76(9), pp. 715-723.

Reeder et al., 1978, "Dentin Permeability: Determinants of Hydraulic Conductance," J. Dent. Res., 57(2):187-193.

Schiff et al., 1994, "Efficacy of a dentifrice containing potassium nitrate, soluble pyrophosphate, PVM/MA copolymer, and sodium fluoride on dentinal hypersensitivity: a twelve week clinical study," J. Clin. Dent., 5 Spec No, pp. 87-92.

Thau et al., 1965, "A New Procedure for the Preparation of Polyethylene-Mineral Oil Gels," J. Soc. Cosmetic Chemists, vol. 16, pp. 359-363.

Database WPI Week 200514 Thomson Scientific, London, GB: AN2005-127329 XP002506831 & JP 2005-029484A (KAO Corp.) Feb. 3, 2005 Abstract.

International Search Report for corresponding International Application No. PCT/US2010/039677, mailed May 11, 2011.

International Search Report for International Application No. PCT/US2010/061324, mailed Oct. 27, 2011.

International Search Report for International Application No. PCT/US2008/058704, mailed Jan. 13, 2009.

Ye Jin and Hak-Kong Yip, "Supragingival Calculus: Formation and Control," International and American Associations for Dental Research 13(5):426-441 (2002).

* cited by examiner

THERAPEUTIC ORAL COMPOSITION

BACKGROUND OF THE INVENTION

The three mineralized tissues of teeth are enamel, cementum and dentine. In human teeth, enamel covers the crown dentine whereas cementum covers the root dentine. In turn, the dentine encloses the pulp of the tooth which provides the dentine with vascular and neural support. Unlike enamel and cementum, the dentine is transversed by numerous tubules. The tubule walls are comprised of the calcified matrix of the dentine and the tubule space is filled with fluid (dentinal fluid) derived from pulp tissue fluid and serum. The matrix mineral is comprised mainly of the calcium phosphate salt, hydroxyapatite, which is poorly soluble at neutral and alkaline pH, and progressively more soluble as the pH becomes progressively more acidic.

Because of their rigid walls, the fluid that fills the narrow dentinal tubules enables cold, tactile, evaporative and osmotic stimuli to be transmitted through the dentine to the pulp in the form of fluid movement. This movement of dentinal fluid is sensed as sharp pain of short duration. This pain is elicited when the odontoblasts that protrude into the pulpal ends of the tubules are disturbed and as a result, the mechano-receptors of the pulpal nerve fibers attached thereto are stimulated. The neural response is usually referred to as dentinal pain and the involved dentine as hypersensitive dentine.

Dentinal hypersensitivity results when protective enamel or cementum covering dentine is lost. Cementum is easier to breach than enamel, because cementum is thinner and more easily eroded by acids. However, breach of cementum cannot happen until there is gingival recession and exposure of the root surface to the oral milieu. Individuals with breached cementum and suffering with dentinal hypersensitivity often experience pain when the exposed area of the tooth comes into contact with cold air or hot and cold liquids or foods that are sweet or acidic or is touched with a metal object.

One way that loss of cementum occurs (and the same is true of enamel) is by the process of dental caries. Acids are produced as end-products of the bacterial degradation of fermentable carbohydrate and these acids dissolve hydroxyapatite, which, like dentine and enamel, is the main calcium phosphate mineral that comprises most of the mineral of the cementum. Another source is acidic foods which, if ingested frequently and for prolonged periods of time, will cause tooth demineralization. These include fruit juices and many beverages, both alcoholic and non-alcoholic. Other acidic agents leading to chemical erosion include various oral personal care products. Amongst these are many of the commercially available mouthwashes and some toothpastes. Abrasive toothpastes and vigorous brushing can aid the erosion process. Another way in which dentinal tubules lose their protective cementum and enamel coverings is through procedures performed by the dentist or hygienist in the dental office. This includes cavity and crown preparation of teeth for fillings and other restorations. It also includes cementum removal during scaling and root planing by the periodontist or dental hygienist.

Many attempts have been made with limited success to plug exposed dentinal tubules and to thereby reduce or stop the ability of stimuli to reach the pulp and cause pain. Materials either singly or in combination have been tried to produce an effective plug. Blockage of the tubules through the formation of a calcium phosphate precipitate is a common approach. This includes the mixing of a soluble calcium salt with a soluble phosphate salt and immediately applying the combination to the open tubules. Alternatively, application of one salt before the other to try to get a precipitate to form within tubules is also used.

Substances other than calcium phosphate also have been utilized. For example, U.S. Pat. No. 3,683,006 describes using potassium, lithium or sodium nitrate. Another example is calcium oxalate particles of small and large size. Application of a protein denaturing agent, such as an alcohol, a surfactant, or a chaotropic salt, can also plug an exposed dentinal tubule since there is protein material within the dentinal tubules and denaturation can sometimes result in partial or complete tubule plugging. Still another but more drastic approach is to place a dental restoration in the affected area or cover the area with an adhesive material. U.S. Pat. No. 5,139,768 describes using a varnish containing strontium salt in a sustained hydrophobic polymer. Adherence without leakage of fluid from the tubules is not always easy to accomplish because adherence to a wet surface is difficult to achieve considering that the continual outward flow or leakage of dentinal fluid from the tubules while a filling or adhesive is setting is hard to stop.

Attempts to treat tooth sensitivity other than by plugging have involved depolarization of the nerve fiber membranes essential for nerve impulse transmission. Potassium salts, especially potassium nitrate, have been largely used for this purpose. For example, U.S. Pat. Nos. 4,751,072 and 4,631,185 describe using potassium bicarbonate and potassium chloride. U.S. Pat. No. 6,524,558 discloses an oral composition containing arginine and a calcium salt to treat dentinal hypersensitivity.

Arginine and other basic amino acids have been proposed for use in oral care and are believed to have significant benefits in combating cavity formation and tooth sensitivity. Combining these basic amino acids with minerals having oral care benefits, e.g., fluoride and calcium, to form an oral care product having acceptable long term stability, however, has proven challenging. In particular, the basic amino acid may raise the pH and facilitate dissociation of calcium ions that can react with fluoride ions to form an insoluble precipitate. Moreover, the higher pH has the potential to cause irritation. At neutral pH or acidic pH, however, a system utilizing arginine bicarbonate (which the art teaches is preferred) may release carbon dioxide, leading to bloating and bursting of the containers. Moreover, it might be expected that lowering the pH to neutral or acidic conditions would reduce the efficacy of the formulation because the arginine may form an insoluble arginine-calcium complex that has a poorer affinity for the tooth surface, and moreover that lowering the pH would reduce any effect the formulation might have on buffering cariogenic lactic acid in the mouth. Use of antimicrobial agents together with arginine and salts also have posed difficulties. Commercially available arginine-based toothpaste, such as ProClude® and DenClude®, for example, contain arginine bicarbonate and calcium carbonate, but not fluoride nor any antimicrobial agent.

Mouthwash and mouthrinse formulations also are well known in the art. Various formulations include antibacterial agents, flavorants, colorants, sweeteners, breath freshening agents, and the like. While a variety of agents can be included in rinse or wash formulations, their concurrent use may not be possible due to interactivity, adverse reactions among reactive agents, resulting in loss of activity. It would be desirable to provide a mouthwash or mouthrinse composition useful in the treatment of a variety of ailments, including for example, dentinal hypersensitivity, anticaries, bad breath, plaque formation, tartar control, stain prevention/whitening, dry mouth, erosion, gingivitis, etc.

SUMMARY OF THE INVENTION

It is a feature of an embodiment of the invention to provide a therapeutic oral composition useful in the treatment of dentinal hypersensitivity, anticaries, bad breath, plaque formation, tartar control, stain prevention/whitening, dry mouth, erosion, gingivitis, etc. It is a feature of the invention to provide a composition that can achieve intrinsic blockage of dentinal tubes, e.g., by taking advantage of the presence of calcium and phosphate ions in dentinal fluid, while at the same time provide antibacterial and anti-caries efficacy, ameliorate dry mouth, and treat erosion and gingivitis. It also is a feature of an embodiment of the invention to provide a composition that provides improved hydraulic conductance exhibiting flow reductions greater than about 50%.

In accordance with these and other features of the embodiments, there is provided an oral care composition comprising arginine in free or salt form, a mucoadhesive polymer, and at least one component selected from the group consisting of pyrophosphate compounds, zinc salts, potassium salts, strontium salts, and mixtures thereof. Preferably, the composition is a mouthwash.

Another embodiment of the invention includes a method of one or more of: reducing hypersensitivity of the teeth; reducing or inhibiting formation of dental caries; reducing or inhibiting demineralization and promoting remineralization of the teeth; reducing or inhibiting gingivitis; inhibiting microbial biofilm formation in the oral cavity; reducing accumulation of plaque; treating dry mouth; reducing erosion of the teeth; protecting enamel after erosive challenges; and cleaning and/or whitening the teeth and cleaning the oral cavity, comprising applying to the oral cavity of a patient in need thereof an oral care composition comprising arginine in free or salt form, a mucoadhesive polymer, and at least one component selected from the group consisting of pyrophosphate compounds, zinc salts, potassium salts, strontium salts, and mixtures thereof.

These and other features will be readily apparent from a review of the detailed description of the preferred embodiments that follows.

DETAILED DESCRIPTION

The following definitions and non-limiting guidelines must be considered in reviewing the description of this invention set forth herein. The headings (such as "Background" and "Summary,") and sub-headings (such as "Compositions" and "Methods") used herein are intended only for general organization of topics within the disclosure of the invention, and are not intended to limit the disclosure of the invention or any aspect thereof. In particular, subject matter disclosed in the "Background" may include aspects of technology within the scope of the invention, and may not constitute a recitation of prior art. Subject matter disclosed in the "Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Specific Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. In addition, the compositions and the methods may comprise, consist essentially of, or consist of the elements described therein.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material. The recitation of a specific value herein, whether referring to respective amounts of components, or other features of the embodiments, is intended to denote that value, plus or minus a degree of variability to account for errors in measurements. For example, an amount of 10% may include 9.5% or 10.5%, given the degree of error in measurement that will be appreciated and understood by those having ordinary skill in the art.

As used herein, "antibacterial activity" herein means activity as determined by any generally accepted in vitro or in vivo antibacterial assay or test. "Anti-inflammatory activity" herein means activity as determined by any generally accepted in vitro or in vivo assay or test, for example an assay or test for inhibition of prostaglandin production or cyclooxygenase activity. "Antioxidant activity" herein means activity as determined by any generally accepted in vitro or in vivo antioxidant assay or test.

An "oral surface" herein encompasses any soft or hard surface within the mouth including surfaces of the tongue, hard and soft palate, buccal mucosa, gums and dental surfaces. A "dental surface" herein is a surface of a natural tooth or a hard surface of artificial dentition including a crown, cap, filling, bridge, denture, dental implant and the like. The term "inhibiting" herein with respect to a condition such as inflammation in an oral tissue encompasses prevention, suppression, reduction in extent or severity, or amelioration of the condition.

The oral care composition of the preferred embodiments includes arginine in free or salt form, a mucoadhesive polymer, optionally at least one antibacterial agent, and at least one component selected from the group consisting of pyrophosphate compounds, zinc salts, potassium salts, strontium salts, and mixtures thereof. The composition preferably is in the form of a mouthwash or mouthrinse. In addition to these ingredients, the mouthwash or mouthrinse can include sweeteners, pH ajusters, acids, salts, anti-caries agents, and other conventional mouthwash agents. The compositions preferably are useful in total or complete treatment of the oral cavity, including treatment of hypersensitivity, anticaries, bad breath, plaque formation, tartar control, stain prevention/whitening, dry mouth, erosion, gingivitis, etc.

While not intending on being bound by any theory of operation, the inventors believe that use of the combination of components in the compositions provides enhanced tubule occlusion efficacy with a coating on their surface that delivers and retains beneficial agents to that surface. The compositions provide mucoadhesivity and film-forming properties that can be used to address hypersensitivity, dry mouth, acid resistance, deminerialization, and the like.

The compositions described herein contain arginine in free or salt faun. Suitable arginine compounds, derivatives and salts are disclosed in, for example, U.S. Patent Application Publication Nos. 2005/0031551, 2009/0202465, and 2009/0202454, the disclosures of which are incorporated by reference herein in their entireties. Arginine may be present by itself, and can include arginine, and D and L forms thereof. Arginine also may be present in salt form (or as a derivative of arginine). Any salt of arginine can be used in the invention so long as it is capable of releasing arginine in solution. Suitable arginine salts include salts of arginine and one or more of the following: (a) an acidic polymer; (b) a conjugate acid of an anionic surfactant salt; (c) a polyphosphoric or polyphosphonic acid; or (d) an acidic antimicrobial agent. The arginine salt preferably is a salt of arginine and lauroyl sulfuric acid.

The conjugate acid of an anionic surfactant salt may be selected from (i) water-soluble salts of higher fatty acid monoglyceride monosulfate (e.g., salt of the monosulfated monoglyceride of hydrogenated coconut oil fatty acids such as sodium N-methyl N-cocoyl taurate, sodium cocomoglyceride sulfate); (ii) higher alkyl sulfates, e.g., sodium lauryl sulfate; (iii) higher alkyl-ether sulfates, e.g., of formula $CH_3(CH_2)_mCH_2(OCH_2CH_2)_nOSO_3H$, wherein m is 6-16, e.g., 10, n is 1-6, e.g., 2, 3 or 4, and X is Na or K (for example sodium laureth-2 sulfate $(CH_3(CH_2)_{10}(CH_2(OCH_2CH_2)_2OSO_3Na))$; (iv), higher alkyl aryl sulfonates (such as sodium dodecyl benzene sulfonate (sodium lauryl benzene sulfonate)); (v) higher alkyl sulfoacetates (such as sodium lauryl sulfoacetate (dodecyl sodium sulfoacetate), higher fatty acid esters of 1,2 dihydroxy propane sulfonate. sulfocolaurate (N-2-ethyl laurate potassium sulfoacetamide) and sodium lauryl sarcosinate); (vi) and mixtures thereof, e.g., wherein by "higher alkyl" is meant $C_{6-30}$ alkyl, for example $C_{8-18}$.

The arginine salt may include arginine polyphosphate or polyphosphonate salts, including, for example, a salt of arginine and polyvinyl phosphonic acid, a salt of arginine and a polyphosphoric acid, a salt of arginine and hexametaphosphoric acid, a salt of arginine and pyrophosphoric acid, a salt of arginine and a tripolyphosphate salt, and mixtures thereof.

The arginine salt also may include salts of arginine and an antibacterial acid. In a particularly preferred embodiment the invention provides salts of arginine and a benzoic acid optionally substituted with carboxy and/or one or more, e.g., 1, 2, or 3 hydroxys, e.g., benzoic acid, phthalic acid, salicylic acid or trihydroxybenzoic acid, for example, gallic acid.

The arginine in free or salt form may be present in the compositions described herein in an amount of 0.1 wt. % to 20 wt. % of the total composition weight, preferably from 0.25 wt. % to 5 wt. % of the total composition weight, for example from 0.4% to 2.5%, or from 0.5% to 2%, or from 0.6% to 1%, or from 0.75% to 0.9% by weight, based on the total weight of the composition.

The compositions of the present invention also contain a mucoadhesive polymer. Mucoadhesive polymers generally are known and may be selected from one or more of an orally acceptable polyvinylmethylether/maleic anhydride (PVME/MA) copolymer, acrylic acid/methylacrylate/styrene/2-acryloamido-2-methylpropane sulfonic acid copolymer (Lupasol FF4243/Lupasol DVFR), poly(vinylpyrrolidone) (PVP), carboxymethylcellulose (CMC), xanthan, and mixtures thereof. The mucoadhesive polymer preferably is present in an amount of from 0.1% to 20%, for example from 0.25% to 10% by weight, more preferably from 0.4% to 2.5%, or from 0.5% to 2%, or from 0.6% to 1% by weight, based on the total weight of the composition.

Preferred mucoadhesive polymers are those that enhance the delivery and retention of the agents to, and retention thereof on oral surfaces. Such agents useful in the present invention are disclosed in U.S. Pat. Nos. 5,188,821 and 5,192,531. Suitable polyvinylmethylether/maleic anhydride (PVME/MA) copolymers include those in which the methyl vinyl ether to maleic anhydride ratio in the copolymer is from 1:4 to 4:1, and the copolymer has an average molecular weight of 30,000 to 1,000,000, for example 30,000 to 500,000. Preferred PVME/MA copolymers include those under the GANTREZ® brand from ISP (Bound Brook, N.J., 08805). The PVME/MA copolymer may also act as an antibacterial enhancing agent if present in an antibacterial enhancing effective amount. The GANTREZ® copolymers may include, for example, GANTREZ® AN 139 (M.W. 500,000), GANTREZ® AN 119 (M.W. 250,000) and preferably GANTREZ®S-97 Pharmaceutical Grade (M.W. 700, 000) available from ISP Technologies, Inc., Bound Brook, N.J. 08805.

The mucoadhesive polymer useful in the oral care compositions of the invention also include one or more polymers, such as poly(vinylpyrrolidone) (PVP), polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic. 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, the disclosure of which is incorporated herein by reference herein in its entirety. A particularly preferred polymer in this regard is acrylic acid/methylacrylate/styrene/2-acryloamido-2-methylpropane sulfonic acid copolymer (Lupasol FF4243/Lupasol DVFR). Lupasol FF4243 is a copolymer containing 20% acrylic acid, 20% methyl acrylate, 59% 2-acrylamide 2 methylpropanesulfonic acid, and 1% styrene. Another useful class of polymeric agents includes polyamino acids, particularly those containing proportions of anionic surface-active amino acids such as aspartic acid, glutamic acid and phosphoserine, as disclosed in U.S. Pat. No. 4,866,161, the disclosure of which is incorporated herein by reference in its entirety.

The compositions of the preferred embodiments also may optionally contain one or more antibacterial agents. The antibacterial agent may be selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, zinc oxide, stannous salts, copper salts, iron salts), sanguinarine propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing. The antibacterial agent preferably is not triclosan, and may be CPC, chlorhexidine, zinc citrate, zinc oxide, and mixtures thereof. If used, the antibacterial agent preferably is present in an amount of from 0.01% to 10%, for example from 0.025% to 5% by weight, more preferably from 0.05% to 1%, or from 0.075% to 0.5% by weight, based on the total weight of the composition.

The compositions of the preferred embodiments also include at least one or more components selected from the group consisting of pyrophosphate compounds, zinc salts, potassium salts, strontium salts, and mixtures thereof. The pyrophosphate salts useful in the present compositions include the dialkali metal pyrophosphate salts, tetra alkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate. Pyrophosphate ions in different protonated states (e.g., $HP_2O_7^{-3}$) may also exist depending upon the pH of the composition and if part of the tetrasodium pyrophosphate is dissolved. The pyrophosphate salts may be present in an amount ranging from 0.1% to 5% by weight, preferably from 0.2% to 2% by weight, and more preferably from 0.4 to 2% by weight, based on the total weight of the composition. Combinations of pyrophosphate salts may be used.

Zinc salts useful in the embodiments include, for example, any physiologically acceptable zinc compound including water soluble (inclusive of sparingly water soluble) organic and inorganic zinc compounds. The water-soluble zinc compounds (at least 1% soluble) are preferred. Examples of suitable zinc compounds that may be employed include: zinc acetate, zinc fluoride, zinc ammonium sulfate, zinc formate, zinc bromide, zinc iodide, zinc chloride, zinc oxide, zinc nitrate, zinc chromate, zinc phenol sulfonate, zinc citrate, zinc salicylate, zinc dithionate, zinc sulfate, zinc fluosilicate, zinc gluconate, zinc tartarate, zinc succinate, zinc glycerophosphate, and mixtures thereof. Other zinc compounds disclosed in U.S. Pat. No. 4,138,477 having a solubility of a least about 0.01 mg of zinc ions per ml water are incorporated by reference. The zinc salts may be present in amounts within the range of from 0.01-5% by weight, more preferably from 0.1-1% of zinc salt weight, based on the total weight of the composition.

Suitable nitrate and carbonate salts include, for example, any physiologically acceptable salts for use in mouth rinse formulations. Nitrates include the aforementioned zinc nitrate, as well as potassium and sodium nitrates. Suitable carbonates include, for example, calcium carbonate, alkali metal carbonate salts, sodium carbonate, and the like. The nitrate and carbonate salts typically are present in the compositin in an amount of from 0.1% to 30%, preferably from 1% to 10%, and more preferably from 1.5% to 5%, by weight of the present composition.

In addition to the arginine, mucoadhesive polymer, and salts, the oral compositions described in accordance with the embodiments may contain conventional ingredients typically used in oral compositions. For example, liquid mouthwashes may contain solvents such as distilled or deionized water and ethanol; a sweetening agent such as saccharine, aspartame, sorbitol, mannitol, and xylitol; and a flavoring agent such as peppermint oil and spearmint oil (see U.S. Pat. Nos. 4,226,851 and 4,606,912, the disclosures of which are incorporated by reference in their entirety). Dentifrices may contain, for example, a conventional abrasive such as resins, silica, and insoluble alkali metal metaphosphates in a standard amount of 20% to 60% by weight; a binder such as hydroxyethylcellulose, xanthan gum, and sodium carboxymethylcellulose in a standard amount ranging from 0.05% to 5.0% by weight; a foaming agent such as sodium lauryl sulfate, sodium coconut monoglyceride sulfonate, and sodium-N-methyl-N-palmitoyl taurine in a standard amount ranging from 0.5% to 3.0% by weight; a flavoring agent; a sweetening agent; an antiseptic agent and any other ingredient required for the particular composition as recognized by those skilled in the art (see U.S. Pat. Nos. 4,177,258 and 4,721,614, the disclosures of which are incorporated by reference in their entirety). Tablets and powders may contain, for example, a vehicle such as lactose and mannitol, a binder such as corn starch and carboxymethylcellulose, and a disintegrator.

A dentifrice or paste for localized application to a sensitive tooth site such as breeched cementum of an orally exposed root surface may be one that is simpler in composition and applied with a soft applicator. Such a dentifrice or paste may or may not contain conventional abrasive, foaming agent, and flavoring agents. Localized sites such as the dentine following tooth preparation for a dental restoration also involve simpler compositions and include fillers used in dental pulp cappings, cavity liners and cements and any other ingredients required for the composition by those skilled in the art (Craig et al., 1989, Restorative Dental Materials. Mosby, St. Louis, pp. 189-225). For example, zinc oxide and eugenol at levels of (20 and 25%, respectively) would be appropriate for dental cement compositions.

The present embodiments further provide an article of manufacture that includes packaging material and the oral compositions described herein contained within the packaging material. The oral composition is effective in retarding or preventing dentinal hypersensitivity. The packaging material preferably contains a label that indicates that the oral composition is effective in retarding or preventing dentinal hypersensitivity. The packaging material used to contain the oral compositions may induce glass, plastic, metal or any other suitably inert material. For example, a dentifrice containing the oral composition may be contained in a collapsible tube, typically aluminum, lead-lined, or plastic, or a squeeze pump or pressurized dispenser to measure out the contents, or in a tearable sachet. The compositions also may be included in a plastic bottle typically used for dispensing liquids.

The oral composition of the embodiments also may be used in a prophylaxis paste for polishing teeth or treating sensitive teeth or preventing the development of sensitive teeth after scaling, root planing or stain removal by a dentist or hygienist, in a small dental container, such as a tub of a size that permits easy access of the rotary attachments used in dental offices on dental hand-pieces.

An oral care composition of the present invention can take any liquid or gel form suitable for application to an oral surface. In various illustrative embodiments the composition can be a liquid solution suitable for irrigating, rinsing or spraying; a dentifrice such as a dental gel; a periodontal gel; a liquid suitable for painting a dental surface (e.g., a liquid whitener); a mouthrinse, a foam; etc. The composition can contain active and/or carrier ingredients additional to those recited above.

Preferred oral care compositions include those selected from dentifrices, oral rinses, oral strips, lozenges, beads, liposomes, micelles, reverse micelles, micro- or nano-encapsulated containers, enzymes, proteins, gels, sol-gels, hydrogels, silicas, organic zeolites, inorganic silicas such as those present in dentifrice, paint-ons, oral patches, polymers, sprays, smoke inhalatation devices, foams, chewing gums, from the back or through a toothbrush head, oils or other products used for oral hygiene or benefit. These products can also include food stuffs, liquids and probiotics that endogenously contain or can be laced with photoabsorbing species for oral treatment.

In various embodiments, the compositions comprise an orally acceptable source of fluoride ions, which serves as an anticaries agent. One or more such sources can be present. Suitable sources of fluoride ions include fluoride, monofluorophosphate and fluorosilicate salts as well as amine fluorides, including olaflur (N'-octadecyltrimethylendiamine-N, N,N-tris(2-ethanol)-dihydrofluoride) and stannous fluoride. Other anticaries agents can be used, such as arginine and arginine derivatives (e.g., ethyl lauroyl arginine (ELAH)).

As anticaries agent, one or more fluoride-releasing salts are optionally present in an amount providing a total of 100 to 20,000 ppm, 200 to 5,000 ppm, or 500 to 2,500 ppm, fluoride ions. Where sodium fluoride is the sole fluoride-releasing salt present, illustratively an amount of 0.01% to 5%, 0.02% to 1% or 0.04% to 0.5%, sodium fluoride by weight can be present in the composition.

Phenolic compounds may be used, and include, subject to determination of oral acceptability, those identified as having anti-inflammatory activity by Dewhirst (1980), Prostaglandins 20(2), 209-222, but are not limited thereto. Examples of antibacterial phenolic compounds include 4-allylcatechol, p-hydroxybenzoic acid esters including benzylparaben, butylparaben, ethylparaben, methylparaben and propylparaben, 2-benzylphenol, butylated hydroxyanisole, butylated hydroxytoluene, capsaicin, carvacrol, creosol, eugenol, guaiacol, halogenated bisphenolics including hexachlorophene and bromochlorophene, 4-hexylresorcinol, 8-hydroxyquinoline and salts thereof, salicylic acid esters including menthyl salicylate, methyl salicylate and phenyl salicylate, phenol, pyrocatechol, salicylanilide, and thymol. These phenolic compounds typically are present in one or more of the natural extracts described above.

In another embodiment the composition comprises an orally acceptable stannous ion source useful, for example, in helping reduce gingivitis, plaque, calculus, caries or sensitivity. One or more such sources can be present. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of 0.01% to 5%, for example 0.03% to 2% or 0.05% to 1% by weight of the composition.

In another embodiment the composition comprises an orally acceptable breath-freshening agent. One or more such agents can be present in a breath-freshening effective total amount. Suitable breath-freshening agents include without limitation zinc salts such as zinc gluconate, zinc citrate and zinc chlorite, α-ionone and the like.

In another embodiment the composition comprises an orally acceptable antiplaque, including plaque disrupting, agent. One or more such agents can be present in an antiplaque effective total amount. Suitable antiplaque agents include without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and chelating agents such as citric and tartaric acids and alkali metal salts thereof.

In another embodiment the composition comprises an orally acceptable anti-inflammatory agent. One or more such agents can be present in an anti-inflammatory effective total amount. Suitable anti-inflammatory agents include without limitation steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone. One or more anti-inflammatory agents are optionally present in the composition in an anti-inflammatory effective amount.

Compositions of the inventions optionally contain other ingredients such as enzymes, vitamins and anti-adhesion agents. Enzymes such as proteases can be added for anti-stain and other effects. Non-limiting examples of vitamins include vitamin C, vitamin E, vitamin B5, and folic acid. In various embodiments, the vitamins have antioxidant properties. Anti-adhesion agents include ethyl lauroyl arginine (ELAH), solbrol, ficin, silicone polymers and derivatives, and quorum sensing inhibitors.

Among useful carriers for optional inclusion in a composition of the invention are diluents, abrasives, bicarbonate salts, pH modifying agents, surfactants, foam modulators, thickening agents, viscosity modifiers, humectants, sweeteners, flavorants and colorants. One carrier material, or more than one carrier material of the same or different classes, can optionally be present. Carriers should be selected for compatibility with each other and with other ingredients of the composition.

Water is a preferred diluent and in some compositions such as mouthwashes and whitening liquids is commonly accompanied by an alcohol, e.g., ethanol. The weight ratio of water to alcohol in a mouthwash composition is generally 1:1 to 20:1, for example 3:1 to 20:1 or 4:1 to 10:1. In a whitening liquid, the weight ratio of water to alcohol can be within or below the above ranges, for example 1:10 to 2:1.

In a still further embodiment a composition of the invention comprises at least one pH modifying agent. Such agents include acidifying agents to lower pH, basifying agents to raise pH and buffering agents to control pH within a desired range. For example, one or more compounds selected from acidifying, basifying and buffering agents can be included to provide a pH of 2 to 10, or in various illustrative embodiments 2 to 8, 3 to 9, 4 to 8, 5 to 7, 6 to 10, 7 to 9, etc. Any orally acceptable pH modifying agent can be used, including without limitation carboxylic, phosphoric and sulfonic acids, acid salts (e.g., monosodium citrate, disodium citrate, monosodium malate, etc.), citric acids, alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an orally acceptable pH range.

In a still further embodiment a composition of the invention comprises at least one surfactant, useful for example to compatibilize other components of the composition and thereby provide enhanced stability, to help in cleaning the dental surface through detergency, and to provide foam upon agitation, e.g., during brushing with a dentifrice composition of the invention. Any orally acceptable surfactant, most of which are anionic, nonionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of 0.01% to 10%, for example 0.05% to 5% or 0.1% to 2% by weight of the composition.

In a still further embodiment a composition of the invention comprises at least one foam modulator, useful for example to increase amount, thickness or stability of foam generated by the composition upon agitation. Any orally acceptable foam modulator can be used, including without limitation polyethylene glycols (PEGs), also known as polyoxyethylenes. High molecular weight PEGs are suitable, including those having an average molecular weight of about 200,000 to about 7,000,000, for example about 500,000 to about 5,000,000 or about 1,000,000 to about 2,500,000. One or more PEGs are optionally present in a total amount of about 0.1% to about 10%, for example about 0.2% to about 5% or about 0.25% to about 2% by weight of the composition.

In a still further embodiment a composition described herein may comprise at least one thickening agent, useful for example to impart a desired consistency and/or mouth feel to the composition. Any orally acceptable thickening agent can be used, including without limitation carbomers, also known as carboxyvinyl polymers, carrageenans, also known as Irish moss and more particularly t-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. A preferred class of thickening or gelling agents includes a class of homopolymers of acrylic acid crosslinked with an alkyl ether of pentaerythritol or an alkyl ether of sucrose, or carbomers. Carbomers are commercially available from B. F. Goodrich as the Carbopol® series. Particularly preferred Carbopols include Carbopol 934, 940, 941, 956, 974P, and mixtures thereof. One or more thickening agents are optionally present in a total amount of 0.01% to 15%, for example 0.1% to 10% or 0.2% to 5% by weight of the composition.

In a still further embodiment, the composition may include at least one viscosity modifier, useful for example to inhibit settling or separation of ingredients or to promote redispersibility upon agitation of a liquid composition. Any orally acceptable viscosity modifier can be used, including without limitation mineral oil, petrolatum, clays and organomodified clays, silica and the like. One or more viscosity modifiers are optionally present in a total amount of 0.01% to 10%, for example 0.1% to 5% by weight of the composition.

In a still further embodiment the composition may include at least one humectant, useful for example to prevent hardening of a tooth paste upon exposure to air. Any orally acceptable humectant can be used, including without limitation polyhydric alcohols such as glycerin, sorbitol, xylitol or low molecular weight PEGs. Most humectants also function as sweeteners. One or more humectants are optionally present in a total amount of 1% to 70%, for example 1% to 50%, 2% to 25%, or 5% to 15% by weight of the composition.

In a still further embodiment the composition may include at least one sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, cyclamates and the like. One or more sweeteners are optionally present in a total amount depending strongly on the particular sweetener(s) selected, but typically 0.005% to 5% by weight of the composition.

In a still further embodiment the composition may include at least one flavorant, useful for example to enhance taste of the composition. Any orally acceptable natural or synthetic flavorant can be used, including without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of 0.01% to 5%, for example 0.1% to 2.5% by weight of the composition.

In a still further embodiment the composition may comprise at least one colorant. Colorants herein include pigments, dyes, lakes and agents imparting a particular luster or reflectivity such as pearling agents. A colorant can serve a number of functions, including for example to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount of 0.001% to 20%, for example 0.01% to 10% or 0.1% to 5% by weight of the composition.

In various embodiments, the invention provides chewing gum compositions comprising a gum base and an effective amount of the combination of extracts discussed above. Chewing gum formulations typically contain, in addition, one or more plasticizing agents, at least one sweetening agent and at least one flavoring agent. The chewing gum formulations preferably are prepared using optically clear carriers to provide an optically clear chewing gum composition.

Gum base materials are well known in the art and include natural or synthetic gum bases or mixtures thereof. Representative natural gums or elastomers include chicle, natural rubber, jelutong, balata, guttapercha, lechi caspi, sorva, guttakay, crown gum, and perillo. Synthetic gums or elastomers include butadiene-styrene copolymers, polyisobutylene and isobutylene-isoprene copolymers. The gum base is incorporated in the chewing gum product at a concentration of 10 to 40% and preferably 20 to 35%.

In other embodiments, the oral compositions comprise an edible oral strip comprising one or more polymeric film forming agents and an effective amount of the combination of extracts discussed above. The one or more polymeric film forming agents are selected from the group consisting of orally acceptable polymers such as pullulan, cellulose derivatives, and other soluble polymers including those well-known in the art. Again, the polymer strip preferabl is optically clear.

The embodiments are directed to methods for one or more of the following: reducing hypersensitivity of the teeth; reducing or inhibiting formation of dental caries; reducing or inhibiting demineralization and promoting remineralization of the teeth; reducing or inhibiting gingivitis; inhibiting microbial biofilm formation in the oral cavity; reducing accumulation of plaque; treating dry mouth; reducing erosion of the teeth; protecting enamel after erosive challenges; and cleaning and/or whitening the teeth and cleaning the oral cavity, by applying to the oral cavity an oral composition according to any of the embodiments described herein. It is preferred that the composition be applied to the oral cavity periodically (at least once a day, twice a day, three times a day) for a period of from 1 day to more than 6 months, more preferably for at least 2 weeks.

The preferred embodiments now will be described in more detail with reference to the following non-limiting examples.

SPECIFIC EMBODIMENTS OF THE INVENTION

Example 1

In order to test the desensitizing properties of the compositions described herein, several oral compositions were tested using the method described in U.S. Pat. No. 5,589, 159, the disclosure of which is incorporated by reference herein in its entirety. This method measures the hydraulic conductance of materials, providing an objective reduction in fluid flow that correlates with reduction in fluid flow in dentinal tubules. In this method, intact human molars free from caries and restorations are sectioned perpendicularly to the long axis of the tooth with a metallurgical saw to form thin sections, or discs, from about 0.4 to about 0.8 mm thick.

induced by treating with the experimental compositions can be calculated, and the higher the flow reduction, the greater the occlusion efficacy of the composition. Tubular occlusion is calculated as percentage of flow reduction or permeability reduction ((Baseline flow−Treatment flow/Baseline flow)* 100). It is preferred that the compositions of the invention have flow reduction above 50%, preferably above 56%, and even more preferably above 60%.

Table 1 below includes mouthwash formulations:

TABLE 1

|  | I | II | III | IV | Comp A | Comp B | V | Comp C | VI |
|---|---|---|---|---|---|---|---|---|---|
| Gantrez | 0.65 | 0.65 | 0.65 | 0.65 | — | 0.65 | 0.65 | — | 0.65 |
| Arginine | 0.80 | 0.80 | 0.80 | 0.80 | 0.80 | — | 0.80 | 0.80 | 0.80 |
| Cettylpyridinium Chloride | — | — | — | — | — | — | — | 0.075 | — |
| Polvvinvlpyrrolidone (PVP) | — | — | — | — | — | — | — | — | 0.07 |
| Lupasol FF 4243 | — | — | 1.00 | — | — | — | — | — | — |
| Carboxymethykl cellulose | 0.15 | | | | | | 0.15 | 0.15 | — |
| Xanthan Gum | 0.08 | | | | | | 0.08 | 0.08 | |
| Propylene Glycol | 4.00 | 4.00 | 4.00 | 4.00 | 4.00 | 4.00 | 4.00 | 4.00 | 4.00 |
| Sorbitol | 7.00 | 7.00 | 7.00 | 7.00 | 7.00 | 7.00 | 7.00 | 7.00 | 7.00 |
| Glycerin | 7.00 | 7.00 | 7.00 | 7.00 | 7.00 | 7.00 | 7.00 | 7.00 | 7.00 |
| Sodium benzoate | 0.50 | 0.50 | 0.50 | 0.50 | 0.50 | 0.50 | 0.50 | 0.50 | 0.50 |
| Tetrasodium pyrophosphate | 0.45 | 0.45 | 0.45 | 0.45 | 0.45 | 0.45 | 0.45 | 0.45 | 0.45 |
| Tetrapotassium pyrophosphate | 1.35 | 1.35 | 1.35 | 1.35 | 1.35 | 1.35 | 1.35 | 1.35 | 1.35 |
| PEG 40 | 1.20 | 1.2 | 1.2 | 1.00 | 12 | 1.20 | 1.20 | 1.20 | 1.20 |
| Sodium Fluoride | 0.05 | 0.05 | 0.05 | 0.05 | 0.05 | 0.05 | — | 0.05 | 0.05 |
| Sucralose | 0.001 | 0.001 | 0.001 | 0.001 | 0.001 | 0.001 | 0.001 | 0.001 | 0.001 |
| Saccharin | 0.30 | | 0.30 | — | 0.30 | 0.30 | 0.30 | 0.30 | 0.30 |
| Flavor | 0.20 | 0.20 | 0.20 | 0.15 | 0.20 | 0.20 | 0.20 | 0.20 | 0.20 |
| Zin citrate | — | 0.28 | — | — | — | — | — | — | 0.28 |
| Zinc oxide | — | — | — | — | — | — | 1.00 | 0.50 | — |
| KNO3 | — | 3.00 | 3.00 | 3.00 | — | — | — | — | 3.00 |
| Water | bal. | bal. | bal. | bal. | bal. | bal. | bal. | bal. | bal. |
| Citric acid/NaOH | pH mod. | pH mod. | pH mod. | pH mod. | pH mod. | pH mod. | pH mod. | pH mod. | pH mod. |

Sections containing dentin and free of enamel were selected for testing and then etched with citric acid solution to remove the smear layer. Each disc was mounted into a split chambered device described in *J. Dent. Research*, 57:187 (1978) which is a special leak-proof chamber connected to a pressurized fluid reservoir containing a tissue culture fluid. By using a mixture of pressurized nitrogen and carbon dioxide gas, the fluid can be made at physiological pH. To further ensure accuracy, the discs were wetted with artificial saliva (phosphate buffer saline, PBS) to approximate intra-oral conditions. The apparatus includes a glass capillary tube attached to a flow sensor (FLODEC, DeMarco Engineering SA, Geneva). An air bubble is injected into the glass capillary tube. By measuring the displacement of the bubble as a function of time, fluid flow through the dentin disc can be measured. Fluid flow is equivalent to the dentin permeability.

Dentin permeability is measured before (baseline) and after the mouthwash application. Baseline measurement reflects maximum tubular openness which results in higher permeability. Following measurement of the baseline fluid flow in the dentin disc, 400 uL of the compositions were applied to the external surface with a micropipette. After a period of 10 minutes, the compositions were rinsed off the surface 6 times with 400 uL PBS. The percent flow reduction The hydraulic conductance of samples I-IV, and Comparison A and Comparison B were measured. The values are reported in Table 2 below.

TABLE 2

| Sample | I | II | III | IV | Comp. A | Comp. B |
|---|---|---|---|---|---|---|
| Flow Reduction | 68 | 61 | 64 | 65 | 49 | 43 |

The above table reveals that the inventive compositions provided superior flow reduction, when compared to comparative mouthrinses A and B. While all of the samples exhibited occlusion efficacy with flow reductions above 40%, the inventive samples all had hydraulic conductance flow reduction of greater than 60%. These examples reveal that the inventive compositions provide superior results.

Example 2

Additional mouthrinse formulations (Table 3) were prepared, varying the types of salts employed, as well as the presence or absence of mucoadhesive polymer and arginine.

TABLE 3

|  | Comp D | Comp E | Comp F | Comp G | VII | VIII | Comp H |
|---|---|---|---|---|---|---|---|
| Gantrez |  | 0.65 | 0.65 |  | 0.65 | 0.65 |  |
| Arginine | 0.80 |  | 0.80 |  | 0.80 | 0.80 |  |
| Cettylpyridinium Chloride | — | — | — | — | — | — |  |
| Polyvinylpyrrolidone (PVP) | — | — | — | — | — | — |  |
| Lupasol FF 4243* |  |  |  |  |  |  | — |
| Carboxymethykl cellulose |  |  |  |  |  |  | 0.15 |
| Xanthan Gum |  |  |  |  |  |  | 0.08 |
| Propylene Glycol | 4.00 | 4.00 | 4.00 | 4.00 | 4.00 | 4.00 | 4.00 |
| Sorbitol | 7.00 | 7.00 | 7.00 | 7.00 | 7.00 | 7.00 | 7.00 |
| Glycerin | 7.00 | 7.00 | 7.00 | 7.00 | 7.00 | 7.00 | 7.00 |
| Preservative | 0.50 | 0.50 | 0.50 | 0.50 | 0.50 | 0.50 | 0.50 |
| Tetrasodium pyrophosphate | 0.45 | 0.45 |  | 0.45 | 0.45 | 0.45 |  |
| Tetrapotassium pyrophosphate | 1.35 | 1.35 |  | 1.35 | 1.35 | 1.35 |  |
| PEG 40 | 1.20 | 1.2 | 1.2 | 1.00 | 12 | 1.20 | 1.20 |
| Sodium Fluoride** | — | — | 0.05 | 0.05 | 0.05 | 0.05 | 0.05 |
| Sucralose | 0.001 | 0.001 | 0.001 | 0.001 | 0.001 | 0.001 | 0.001 |
| Saccharin | 0.30 | 0.30 |  |  | 0.30 | 0.30 | 0.30 |
| Flavor | 0.20 | 0.20 | 0.20 | 0.15 | 0.20 | 0.20 | 0.20 |
| Zin citrate | — | — | — | — | — | — | — |
| Zinc oxide | — |  | — |  | — | — |  |
| KNO3 | — | — | — | — | — | — |  |
| Calcium Carbonate |  |  |  |  |  | 0.004 |  |
| Water | balance | balance | balance | balance | balance | balance | balance |
| Citric acid/NaOH | pH adjuster | pH adjuster | pH adjuster | PH adjuster | pH adjuster | pH adjuster | pH adjuster |
| Sodium Hydroxide | pH adjuster | pH adjuster | pH adjuster | pH adjuster | pH adjuster | pH adjuster | pH adjuster |

The hydraulic conductance of each of these samples was measured, and the results are shown in Table 4 below.

TABLE 4

| Sample | Ingredients | % flow reduction |
|---|---|---|
| Comp D | Arginine | 15 |
| Comp E | Gantrez | 27 |
| Comp F | Arginine/Gantrez | 30 |
| Comp G | Pyro | 36 |
| Comp A (Table 1) | Arg/Pyro | 42 |
| Comp B (Table 1) | Gant/Pyro | 46 |
| VII | Arg/Gant/Pyro | 65 |
| VIII | Arg/Gant/Pyro/Ca | 79 |
|  | Sensodyne Total Gentle Care | 1 |
|  | Listerine Total Care Sensitive | −4 |
| XVI | NaF (control) | 13 |

The data in Table 4 reveal that when a mucoadhesive polymer is combined with arginine (comparative example F) without the addition of salts, similar to the formulations disclosed in the examples of U.S. Patent Application Publication No. 2009/0202454, the hydraulic conductance test provided only a 30% reduction in flow. While comparative examples A and B from table 1 exhibited occlusion efficiency with flow reductions above 40%, the flow reduction was far inferior to the flow reduction achieved in accordance with the present invention. Indeed, Example VII included the addition of pyrophosphate salts, but otherwise was identical to comparative example F. Example VII provided a greater than doubling of the reduction in flow rate, achieving a flow reduction of 65% (compared to only 30% for comparative example F). Similarly, the addition of a minor amount of calcium salts in example VIII (contrasted with the use of large amounts of calcium carbonate abrasives, which would not produce calcium salts), improved the flow reduction even more, achieving a flow reduction of 79%.

The invention has been described above with reference to illustrative Examples, but it is to be understood that the invention is not limited to the disclosed embodiments. Alterations and modifications that would occur to one of skill in the art upon reading the specification are also within the scope of the invention, which is defined in the appended claims.

We claim:

1. An oral care composition comprising
   arginine in free or salt form, wherein the arginine compound is present in an amount within the range of from 0.6% to 1% by weight,
   a mucoadhesive polymer which is a polyvinylmethylether/maleic anhydride (PVME/MA) copolymer,
   a pyrophosphate compound comprising tetrasodium pyrophosphate and tetrapotassium pyrophosphate,
   a zinc salt comprising zinc citrate; and
   wherein the oral care composition is abrasive free.

2. The composition as claimed in claim 1, wherein the arginine compound is present in an amount within the range of from 0.75% to 0.9% by weight.

3. The composition as claimed in claim 1, wherein the polyvinylmethylether/maleic anhydride (PVME/MA) copolymer is present in an amount within the range of from 0.1% to 20% by weight.

4. The composition as claimed in claim 1, further comprising an antibacterial agent.

5. The composition as claimed in claim 1, wherein the composition is in a form selected from the group consisting of a mouthwash, a dental gel, a periodontal gel and a liquid suitable for painting a dental surface.

6. The composition as claimed in claim 5, wherein the composition is a mouthwash.

7. The composition as claimed in claim 1, wherein the composition has a flow reduction above 60%, when measured using a hydraulic conductance test.

8. An article comprising packaging material and the composition as claimed in claim 1, wherein the packaging material comprises a label that indicates the oral composition is effective in retarding dentinal hypersensitivity.

* * * * *